United States Patent
Gaillard et al.

(10) Patent No.: US 8,256,132 B2
(45) Date of Patent: *Sep. 4, 2012

(54) SILENCER FOR DRYING APPLIANCE AND SILENT HAIR DRYER

(75) Inventors: Christophe Gaillard, Romorantin-Lanthenay (FR); Michel Guillosson, Olivet (FR); Roland Quessard, Romorantin-Lanthenay (FR)

(73) Assignee: Velecta Paramount, Romorantin-Lantheray (FR)

( * ) Notice: Subject to any disclaimer, the term of this patent is extended or adjusted under 35 U.S.C. 154(b) by 1118 days.

This patent is subject to a terminal disclaimer.

(21) Appl. No.: 12/048,810

(22) Filed: Mar. 14, 2008

(65) Prior Publication Data
US 2009/0188126 A1     Jul. 30, 2009

(30) Foreign Application Priority Data
Jan. 25, 2008  (FR) ...................................... 08 00396

(51) Int. Cl.
A45D 20/00     (2006.01)

(52) U.S. Cl. ....... 34/95; 34/96; 34/97; 34/100; 132/221; 181/269; 415/119; 39/384

(58) Field of Classification Search ................ 34/80, 86, 34/90, 95, 96, 97, 98, 99, 100; 132/200, 132/221; 181/269; 415/119; 39/384
See application file for complete search history.

(56) References Cited

U.S. PATENT DOCUMENTS

| | | | | |
|---|---|---|---|---|
| 5,810,911 A | * | 9/1998 | Behrendt et al. | 95/278 |
| 6,212,790 B1 | * | 4/2001 | Stetson | 34/97 |
| 2009/0188126 A1 | * | 7/2009 | Gaillard et al. | 34/97 |
| 2011/0016737 A1 | * | 1/2011 | Gaillard et al. | 34/97 |

FOREIGN PATENT DOCUMENTS

| | | |
|---|---|---|
| DE | 31 41 245 A1 | 4/1983 |
| DE | 88 05 910 U1 | 6/1988 |
| EP | 0 631 738 A | 1/1995 |
| JP | 60 135700 A | 7/1985 |
| JP | 07155219 A * | 6/1995 |
| WO | WO 9211783 A1 * | 7/1992 |

* cited by examiner

*Primary Examiner* — Stephen M. Gravini
(74) *Attorney, Agent, or Firm* — Miles & Stockbridge P.C.; Eric G. King

(57) ABSTRACT

A silent hair dryer and a silencer for a hair dryer includes at least one casing with an inlet end and an outlet end and enclosing at least one turbine sucking in air via at least one admission orifice upstream of the turbine and expelling it downstream via at least one outlet orifice. The silent hair dryer includes at least one chamber upstream of the admission orifice and an inlet orifice for aspiration of air upstream of the chamber; the diameter of the chamber being greater than the diameter of the admission orifice and the diameter of the inlet orifice, the length and the diameter of the chamber being of such a size so as to define a volume turned as a function of the sound frequencies to be attenuated by the silencer.

19 Claims, 7 Drawing Sheets

SILENCER FOR DRYING APPLIANCE AND SILENT HAIR DRYER

BACKGROUND

1. Field of the Invention

The present invention relates to the field of drying appliances and, in particular, of hair dryers. The present invention relates more particularly to a silencer for a drying appliance such as a hair dryer, as well as a silent hair dryer.

2. General Background

Dryers, hair dryers in particular, are generally equipped with a fan or a turbine acting as blower. Often, the turbine is the centrifugal type, producing an airflow piped by walls of a casing of the dryer, to a nozzle concentrating the airflow to obtain effective pressure for drying. The drying function is generally improved by the presence of resistance downstream of the fan or turbine, so as to heat the expelled air. The entry of air at the level of the turbine is generally provided by a grille preventing access to the revolving parts of the turbine and protecting the appliance from fouling. This grille often comprises a first part fixed to the air admission bell of the centrifugal turbine and constituted by ribs (or beads) spaced such that they at least prevent penetration by a child's finger and a second part constituted by a filter made of a grille and/or by open-weave foam and whereof the frame is of such a size that it can screen out dust and hair. Often, this filter is made detachable by various solutions such as being inserted into a cover allowing it to be disassembled and reassembled quickly for easy cleaning.

A problem with drying appliances relates to the often high sound level of the motor and of the fan or the turbine. Indeed, the rotations of the motor and of the fan or of the turbine are sources of noise. The noise generated by such appliances is a function of the power of the motor and of the rotation speed of the turbine. This noise is particularly annoying for the user, especially in the case of hair dryers used close to the ears of users.

Solutions for optimising the yield of the centrifugal turbine and attenuating its sound level are known from the prior art. Certain solutions consist in decreasing the air turbulence generated near the blades by radiating the edge of the admission of the air upstream or downstream of the grille and of the dust filter. Certain solutions of the prior art consist of fitting the hair dryer with screens designed to diminish propagation of sound waves radiating perpendicularly to the air admission. Certain screens are made from insulating material and others are in the form of either a casing pierced with lateral air intake inlets, or a cover enclosing the body of the appliance at the level of the turbine such that this air admission occurs annularly between this body and this cover. The drawback to these solutions is that they are unsatisfactory. In fact, to mask the sound effect of the turbulence generated at the leading edge of the blades of the turbine, the flowing section of the air admission must be decreased to the maximum, to the detriment of the airflow yield of the turbine. Attaining the objective of flow is possible only by increasing the speed of the motor, inducing a decrease in the shelf life of the appliance. Also, the sound attenuation gained is then partly lost by the increase in noise generated by the motor. On the other hand, the lateral air intake inlets do not satisfactorily dampen the noise.

Another problem in the field of drying appliances relates to the fact that noise attenuation cannot generally be added to devices already distributed.

In this context, it is interesting to propose a silent hair dryer and a silencer for a drying appliance, such as a hair dryer in particular, for reducing noise emitted by the appliance.

SUMMARY

The aim of the present invention is to eliminate certain disadvantages of the prior art by proposing a silencer for a drying appliance, such as a hair dryer in particular, producing an effective reduction in noise generated.

This aim is attained by a silencer for drying appliances, in particular for a hair dryer, the appliances comprising at least one casing comprising an inlet end, an outlet end and at least one motor driving in rotation at least one turbine sucking in air via at least one admission orifice at the level of the inlet end upstream of the turbine and expelling it downstream via at least one outlet orifice at the level of the outlet end, characterised in that it comprises at least one chamber mounted substantially tightly upstream of the admission orifice and comprising an inlet orifice for aspiration of air upstream of the chamber, the diameter of the chamber being greater than the diameter of the admission orifice and the diameter of the inlet orifice, the length and the diameter of the chamber being of such a size so as to define a volume tuned as a function of the sound frequencies to be attenuated by the silencer.

According to another particular feature, the chamber comprises at least one filter of annular shape and comprising at least one porous material, the annular volume and the porosity index of the filter being tuned as a function of the sound frequencies to be attenuated by the silencer.

According to another particular feature, the chamber comprises several filters of increasing density in the direction of the admission orifice of the turbine, of annular shape and comprising at least one porous material, the annular volume and the porosity indices of the filters being tuned as a function of the sound frequencies to be attenuated by the silencer.

According to another particular feature, the filter(s) substantially fills (or fill) the annular volume of the chamber.

According to another particular feature, the porous material present in the filter(s) is a material having open alveoli.

According to another particular feature, the chamber is cylindrical, tapered or polygonal in cross-section.

According to another particular feature, the silencer comprises fixing arrangements on the casing of the drying appliance, at the level of the inlet end.

According to another particular feature, the silencer is equipped with a cover upstream of the inlet orifice of the chamber, the cover comprising fixing arrangements on the silencer, in the vicinity of the inlet orifice.

According to another particular feature, the cover is fitted with at least one filter.

According to another particular feature, the silencer comprises, on one hand, detachable fixing arrangements on the casing identical to detachable fixing arrangements of the cover on the casing of the drying appliance, at the level of the inlet end, and on the other hand, in the vicinity of the inlet orifice, arrangements for anchoring the fixing arrangements of the cover, such that the silencer can be interposed between the casing and the cover.

According to another particular feature, the silencer is made all in one piece with the casing, at the level of the inlet end.

Another aim of present invention is to eliminate certain disadvantages of the prior art by proposing a silent hair dryer generating little noise.

This aim is attained by a silent hair dryer comprising at least one casing comprising an inlet end, an outlet end and at least one motor driving in rotation at least one turbine sucking in air via at least one admission orifice upstream of the turbine and expelling it via at least one outlet orifice downstream, characterised in that it comprises a silencer according to any, of the preceding claims.

According to another particular feature, the silencer is made all in one piece with the casing, at the level of the inlet end.

According to another particular feature, the silencer is fixed detachably on the casing, at the level of the inlet end.

According to another particular feature, the silent hair dryer comprises a cover fixed detachably on the casing, at the level of the inlet end, by detachable fixing arrangements of the cover, the silencer comprising, on one hand, detachable fixing arrangements on the casing identical to the detachable fixing arrangements of the cover, and on the other hand, in the vicinity of the inlet orifice, arrangements for anchoring fixing arrangements of the cover, such that the silencer can be interposed between the casing and the cover.

According to another particular feature, the silent hair dryer comprises a silent turbine, comprising an admission orifice of reduced diameter so as to decrease the noise generated by the turbine and comprising blades whereof the peripheral end is curved in the direction of the direction of rotation of the turbine so as to improve the pressure generated by the turbine, at least to compensate the flow loss resulting from the decrease in the admission diameter of the turbine.

According to another particular feature, the silent hair dryer comprises an aerodynamic ball placed upstream of the admission of the turbine to minimise air perturbations entering the turbine and reduce the sound level of the hair dryer.

BRIEF DESCRIPTION OF THE DRAWINGS

Other particular features and advantages of the present invention will emerge more clearly from the description hereinbelow, given in reference to the attached diagrams, in which.

DETAILED DESCRIPTION

Figure 5B:
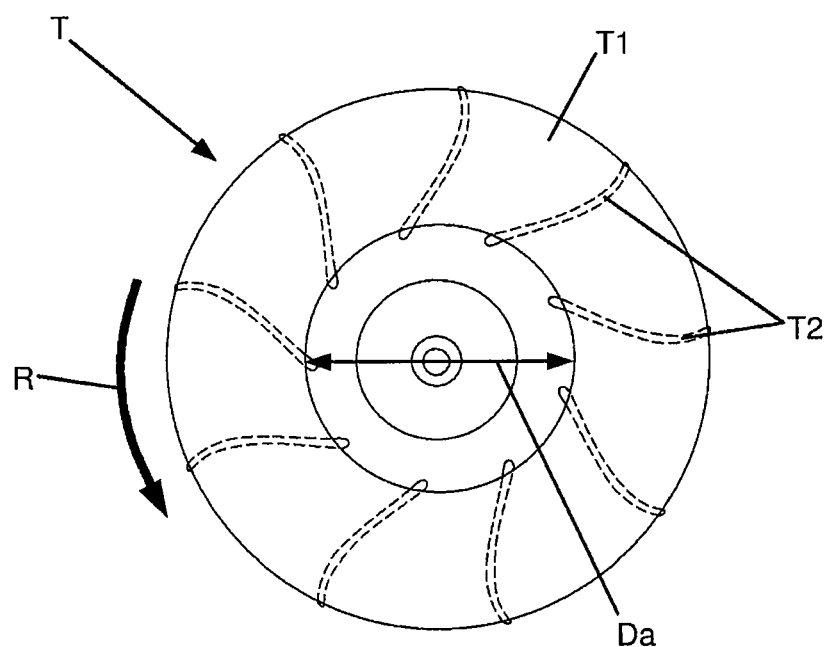
Figure 6A:
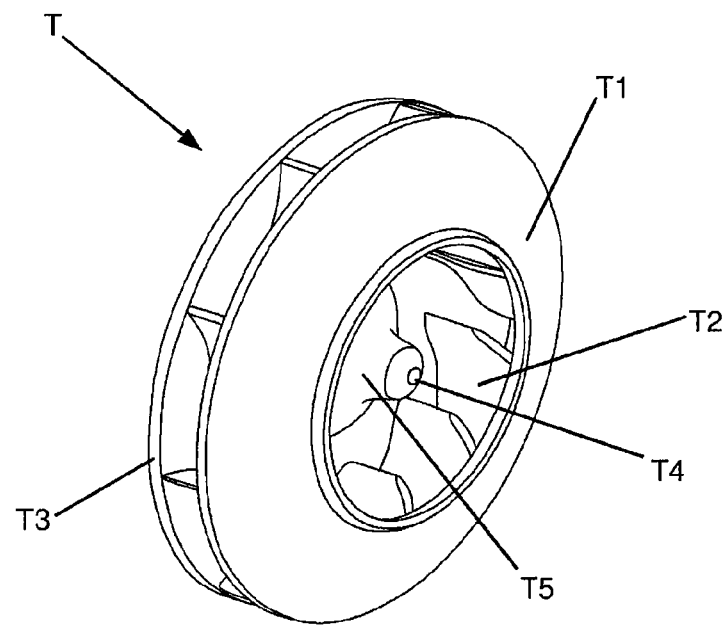
FIGS. 6A and 6B illustrate perspective views of a turbine improved according to certain embodiments of the invention, respectively assembled and in an exploded view.
Figure 6B:
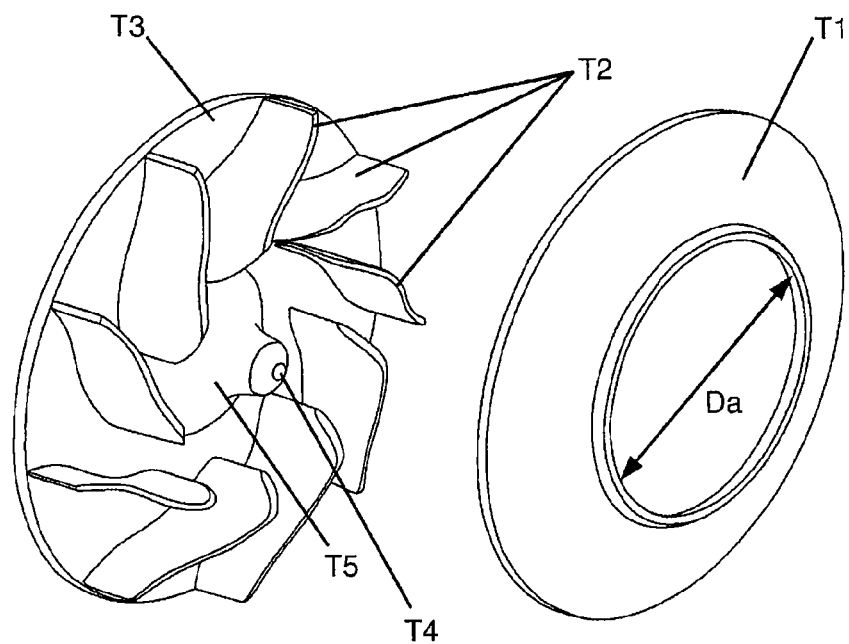
Figure 7:
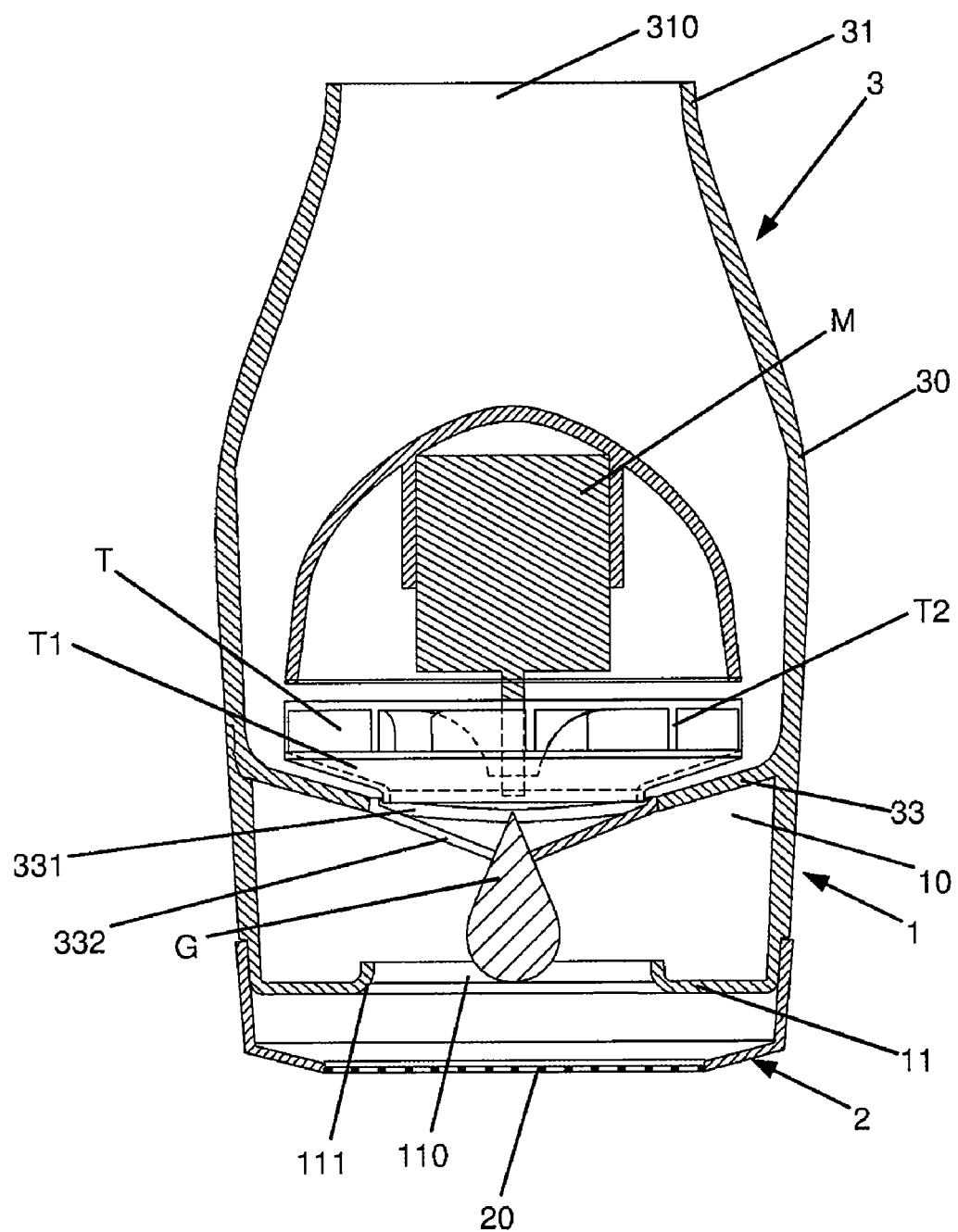
FIG. 7 illustrates a sectional view of a drying appliance fitted with a silencer according to various embodiments of the invention.

The present invention relates to a silencer (1) for drying appliances, in particular for hair dryer (3), and a silent hair dryer. The term drying appliances, or even the term hair dryer, is understood here to mean any type of appliance designed for drying, whether for hair or not. In fact, the invention is adapted to devices and appliances expelling air, heated or not, for example for drying various materials such as, for example, hair. Accordingly, the use which can be made of the invention is not limited to drying of hair. The invention will therefore be limited only to use with an appliance comprising the means or arrangements described herein, or to any adaptation familiar to those skilled in the art. The invention is adapted to any appliance comprising at least one casing (30) having an inlet end (33), an outlet end (31) and at least one motor (M) driving in rotation at least one turbine (T) sucking in air via at least one admission orifice (330) at the level of the inlet end (33) upstream of the turbine (T) and expelling it downstream via at least one outlet orifice (310) at the level of the outlet end (31). This type of appliance drives an airflow (F) through the casing (30), as particularly visible in FIG. 2. This aspirated airflow (F) passes through the inlet (110) and admission (330) orifices, through the silencer (1) which reduces its noise as explained hereinbelow, then passes via the centrifugal turbine which expels it peripherally, between the casing (30) of the appliance and the motor casing (CM). The airflow can of course be heated by a heating device downstream of the turbine, prior to exiting via the outlet orifice (310). As is known from the prior art, the admission orifice (330) can be fitted with a grille (332, FIG. 7) preventing insertion of a child's finger at level of the turbine. This grille can naturally have various shapes and the example of the grille (332) described hereinbelow in FIG. 7 is merely illustrative and in no way limiting. Similarly, as is known from the prior art, the outlet orifice (310) at the level of the discharge end (31) can be fitted with a nozzle concentrating the airflow to boost pressure as it leaves the appliance. In the embodiments shown in the figures, this is a centrifugal turbine creating an airflow (F) generated around the turbine and the motor and piped by the internal walls of the casing (30), though the invention is not limited to this type of arrangement. On the other hand, the turbine (T) illustrated in the figures and particularly visible in FIGS. 5B, 6A and 6B is an example of embodiment of the invention particularly advantageous, but other types of turbines can be utilised, even though the type of turbine described hereinbelow in reference to FIGS. 5B, 6A and 6B is particularly adapted to the principal aim of the invention which is the reduction of noise. Finally, the admission orifice (330) can, according to various embodiments, be arranged in a straight wall at the level of the inlet end (33) or in a tapered wall, as illustrated in the figures. It is evident here that the admission orifice (330) is defined relative to the wall (33) of the inlet end but, in general, the admission relates to the entry of air to the turbine. Therefore, as detailed hereinbelow, when this is a centrifugal turbine (T) comprising a flange (T1) at the level of the air admission in the turbine, as evident particularly in FIGS. 5B, 6A and 6B, the admission orifice important for the aspiration of air and noise generated is in fact the intake orifice of the flange (T1) of the turbine (T), whether the latter is protected or not by a wall (33) of the inlet end. Therefore, in terms here of the admission diameter (Da) of the admission orifice, those of skills in the art will understand that, as a function of the various embodiments detailed hereinbelow, it can be the diameter of the intake orifice of the flange (T1) or the diameter of the admission orifice (330) at the level of the wall (33) in front of the turbine. It is also noted that when the turbine (T) comprises a flange (T1), as illustrated by way of illustration in the figures, and when the turbine is protected by a wall (33) of the inlet end, the flange (T1) and the wall (33) are generally arranged so that the space separating them is sufficiently small to prevent the occurrence of reflux (flowing back) of air exiting from the turbine to the inlet end (33). Also, in these embodiments where the turbine (T) is protected by a wall and comprises a flange (T1), the diameter of the orifice of the wall and the diameter of the entry of the flange are substantially identical, the considerations in diameter being, as explained previously, generally focussed on the entry of air at the level of the turbine (T). Therefore, it can be considered here that the diameter (Da) of the admission orifice (330) corresponds to the inlet diameter of the flange (T1) of the turbine (T) and the two terms are used here in turn to designate the diameter of the air admission in the majority of the embodiments described.

Figure 1:
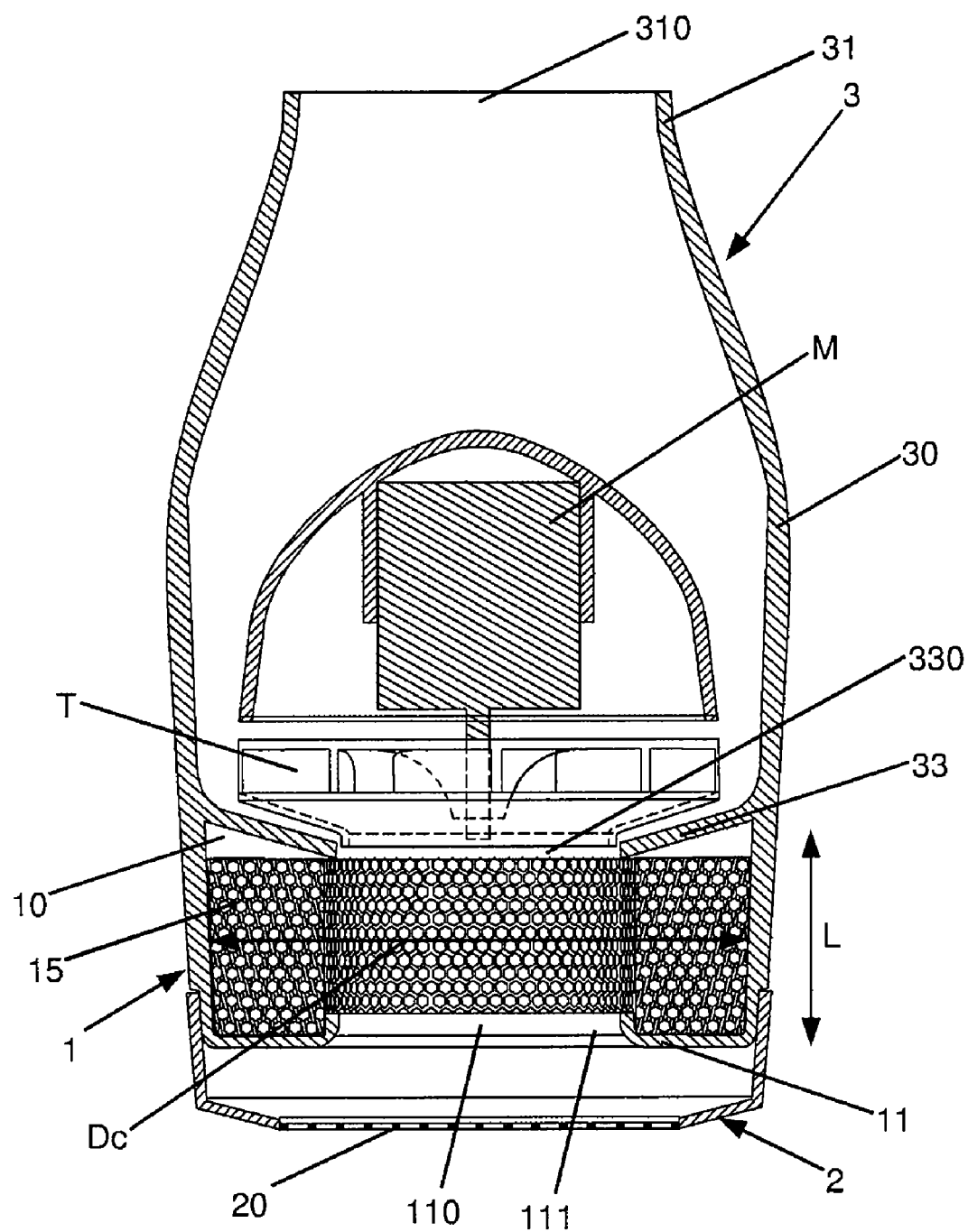
FIG. 1 illustrates a sectional view of a silent drying appliance according to various embodiments of the invention.

The present invention relates to a silencer (1) attenuating noises generated by the motor and the turbine or the fan, as well as a hair dryer (3) comprising at least one silencer (1). The silencer (1) comprises at least one chamber (10) mounted substantially tightly upstream of the admission orifice (330) and comprising an inlet orifice (110) for the aspiration of air upstream of the chamber (10). For instance, this inlet orifice (110) can be arranged in a wall (11) partially closing the silencer. In certain embodiments, this wall (11) comprises a bell (11) whereof the flared edge (111) makes it easy for air to slide to the inside of the chamber (10), thus minimising perturbation. This chamber (10) can, according to various variant embodiments have a cylindrical, tapered or polygonal cross-section or any shape selected by the designers, even though cylindrical or tapered shapes are more aerodynamic and therefore more adapted for use made of them. Similarly, the hair dryer (3), the silencer (1) or all the compartments making it up can naturally have various shapes, even though cylindrical or tapered shapes are preferred. In the present description, the term <<diameter>> of a structure is also understood as the distance (maximum, minimum or average) separating two points situated opposite one another on the structure in question. In general, in the present description, the notion of diameter is utilised to define sizes of airflow sections through an orifice or between two structures. The flow section can of course have any shape circumference since this circumference depends on the structures between which the flow takes place or on the orifice through which the flow takes place. Since the notion of diameter is easily understood in the case of substantially circular structures, the use of this term is understood here in any form which the elements of the invention can assume, such as for example, the hair dryer (3) itself, the chamber (10) or the filter (15) described here. In certain embodiments, the silencer (1) is made all in one piece with the casing (30), at the level of the inlet end (33), as is particularly visible in FIGS. 1 and 3. In other embodiments, the silencer (1) comprises fixing arrangements (35) on the casing (30) of the drying appliance (3), at the level of the inlet end (33), as is particularly visible in FIG. 2. In certain variant embodiments, the silencer is equipped with a cover (2) upstream of the inlet orifice (110) of the chamber (10). As is particularly visible in FIG. 2, the cover (2) comprises fixing arrangements (25) on the silencer (1), in the vicinity of the inlet orifice (110). This cover (2) is fitted with at least one filter (20). As is known per se, this filter can comprise a grille and/or an open-weave (i.e., with open alveoli) material allowing passage of air while filtering particles. In certain variant embodiments, the cover (2) can be made all in one piece with the silencer (1), especially in the case where the silencer (1) is mounted detachably on the casing (30) of the hair dryer (3). In certain particularly advantageous embodiments, the silencer (1) is designed to complement existing hair dryers. In these embodiments, the silencer (1) comprises, on one hand, detachable fixing arrangements (35) on the casing (30) identical to detachable fixing arrangements (25) of the cover (2) on the casing (30) of the drying appliance (3), at the level of the inlet end (33), and on the other hand, in the vicinity of the inlet orifice (110), arrangements for anchoring the fixing arrangements (25) of the cover (2), such that the silencer can be interposed between the casing (30) and the cover (2). Therefore, the silencer (1) can be sold separately to the hair dryer (3), and even be distributed as an add-on to hair dryers (3) already distributed on the market. For instance, there are hair dryers (3) equipped with a removable cover (2) screwed on or fitted on (by a bayonet system) to the inlet end (33) of the hair dryer. The silencer can then include a thread for receiving this cover (2) once unscrewed from the hair dryer (2) and a tapping so that it can be screwed in place of the cover (2). In another example, a more practical use, the silencer can comprise grooves and tenons for cooperating, respectively, with tenons in the hair dryer and the grooves of the cover. Therefore, by simple habitual manipulation (during cleaning for example) the user can improve the hair dryer by adding to it a silencer (1) according to the invention. The invention can therefore provide various forms and dimensions of the silencer (1) for it to be adaptable to various types of hair dryer (3).

Accordingly, the invention also relates to a hair dryer (3) fitted with a silencer according to the invention. In certain embodiments, the silencer (1) is made all in one piece with the casing (30), at the level of the inlet end (33). In other embodiments, the silencer (1) is fixed detachably on the casing (30), at the level of the inlet end (33). In certain embodiments, the silencer is designed to be detachable. In this case, the hair dryer comprises a cover (2) fixed detachably on the casing (30), at the level of the inlet end (33), by detachable fixing arrangements (25) of the cover (2), the silencer (1) comprising, on one hand, detachable fixing arrangements (35) on the casing (30) identical to the detachable fixing arrangements (25) of the cover (2), and on the other hand, in the vicinity of the inlet orifice (110), arrangements for anchoring the fixing arrangements (25) of the cover (2), such that the silencer can be interposed between the casing (30) and the cover (2).

Figure 2:
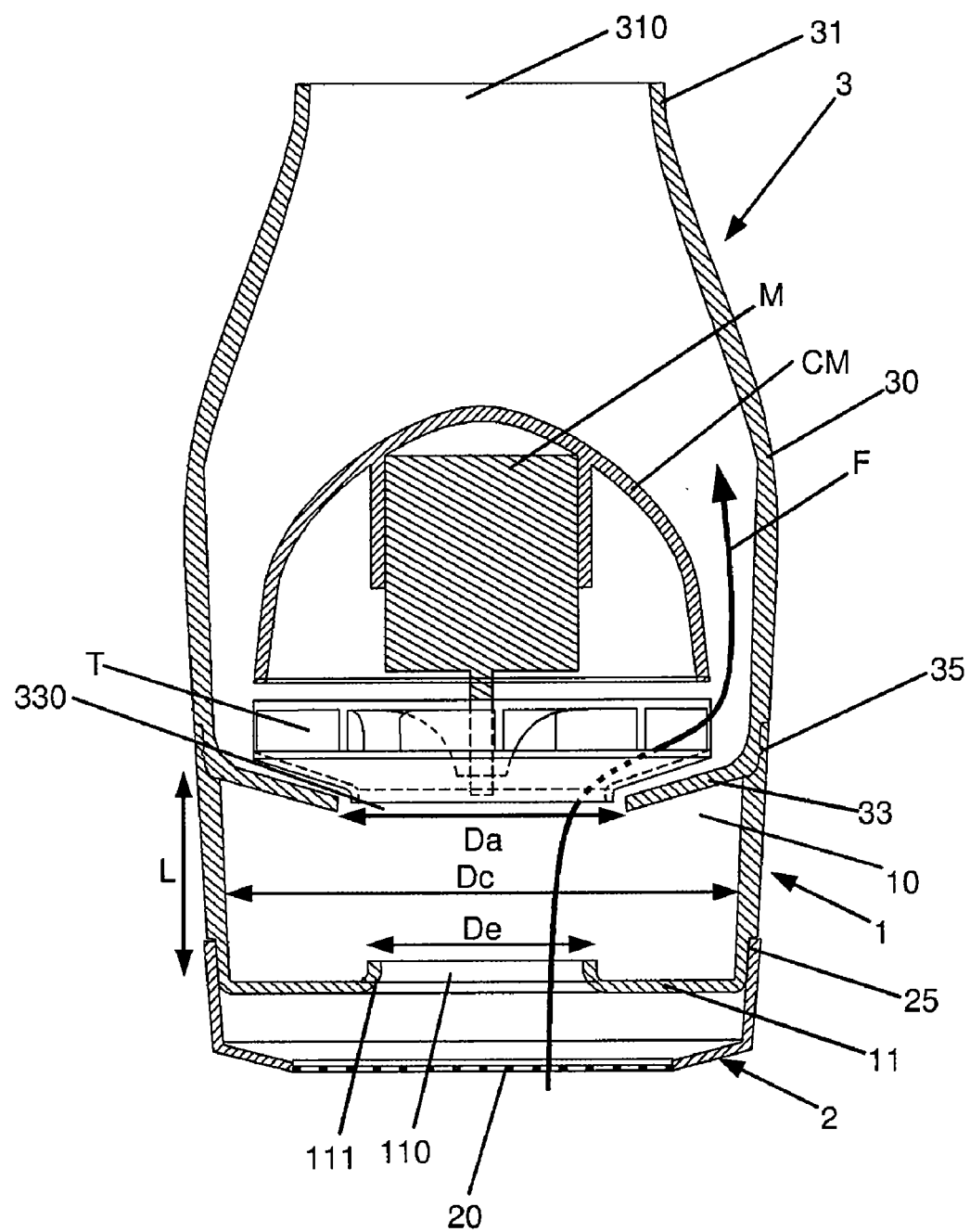
FIG. 2 illustrates a sectional view of a drying appliance fitted with a silencer according to various embodiments of the invention.
Figure 3:
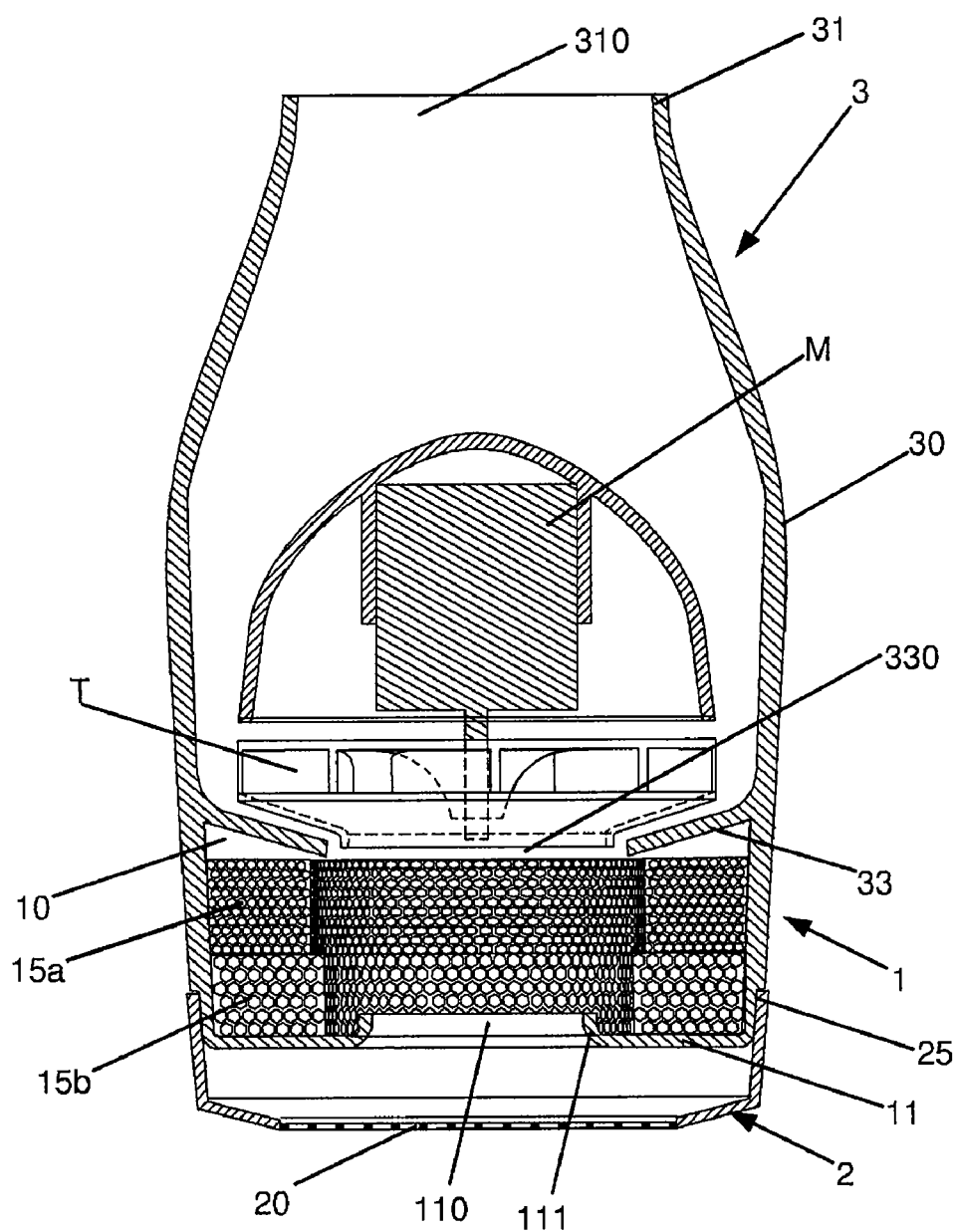
FIG. 3 illustrates a sectional view of a silent drying appliance according to various embodiments of the invention.

More specifically, the chamber (10) of the silencer has a diameter (Dc) greater than the diameter (Da) of the admission orifice (330) (or, equally, of the entry of the flange of the turbine) and of the diameter (De) of the inlet orifice (110). Therefore, the chamber offers an open volume around the airflow for attenuating noise. Also, according to an embodiment of the invention, the diameter (De) of the inlet orifice (110) is less than the diameter (Da) of the admission orifice (330), as is particularly visible in FIGS. 2 and 3, so as to facilitate passage of air and minimise turbulence in the silencer (1) and the hair dryer (3). However, in certain embodiments, these two diameters (Da, De) will be identical, such as for example illustrated in FIG. 1, and in other embodiments the inverse configuration can be considered, even though the configuration illustrated in FIGS. 2 and 3 is more advantageous, since it minimises turbulence and therefore reduces noise. Also, the invention provides an improved turbine detailed hereinbelow in reference to FIGS. 5B, 6A and 6B whereof the inlet diameter (Da) is diminished to minimise noise. These embodiments of the turbines detailed hereinbelow can, in particular and for example, be utilised in embodiments where the admission diameter (Da) in the turbine is substantially identical to the inlet diameter (De) in the silencer. And, the length (L) and the diameter (Dc) of the chamber (10) are of such a size as to define a volume tuned as a function of the sound frequencies to be attenuated by the silencer (1). In fact, the chamber (10) of the silencer (1) according to the invention comprises a volume surrounding (encircling, enclosing) the open passage of airflow through the silencer, thus attenuating noise. The airflow (F) passes through the chamber in its centre, substantially inside a cylinder defined by the smallest diameter of the diameters (Da, De) of the admission orifice (330) and of the inlet orifice (110), though the airflow (F) also reaches the rest of the chamber, in particular an annular volume, defined between the diameter (Dc) of the chamber (10) and at least a diameter of the diameters (Da, De) of the admission orifice (330) and of the inlet orifice (110). The volume of the chamber and in particular this annular volume constitute a sound filter which attenuates the appliance's noise. As a function of the sound frequencies to be attenuated in the appliance on which the silencer is to be installed, the volume of the chamber should have particular dimensions which will be obtained by various combinations of the diameter (Dc) of the chamber and its length (L).

Figure 4:
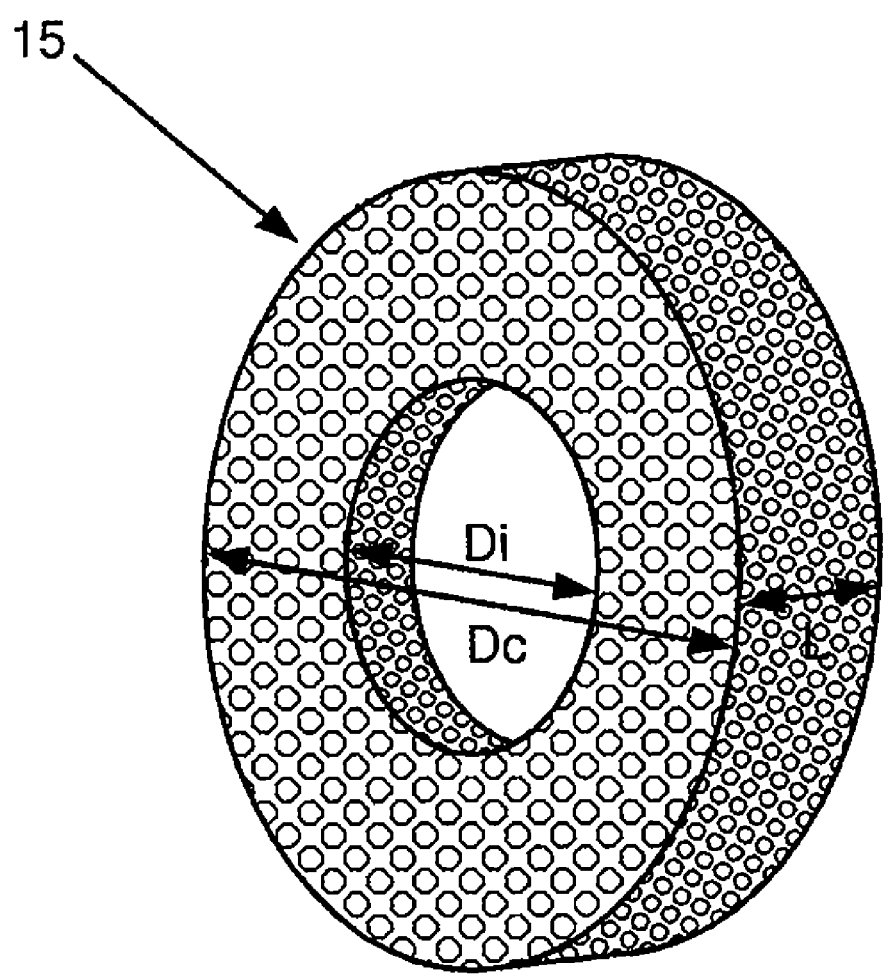
FIG. 4 illustrates a perspective view of a filter made of porous material equipping the devices according to various embodiments of the invention.

In certain particularly advantageous embodiments, the chamber (10) comprises at least one filter (15) of annular shape, as shown in FIG. 4. This annular filter fills the annular volume of the chamber, opened around the passage of the airflow (F) between the inlet and admission orifices and it attenuates noise even better. As illustrated in FIG. 4, this filter has substantially the shape of a ring (the cross-section can vary in shape as a function of the cross-section of the silencer), with an external diameter substantially equal to the diameter of the chamber (Dc) and an internal diameter (Di), for the passage of the airflow (F), substantially equal to at least a diameter of the diameters (Da) of the admission orifice (330) and of the inlet orifice (110). It is noted here that, in certain embodiments, the internal diameter (Di) of the filter(s) (15, 15a, 15b) can be variable over the entire length (L), for example in the case where the diameters of the intake orifice and of the admission orifice are not identical. Therefore, the internal diameter of the filter can fit (follow) the tapered profile described by the diameters of these two orifices. As specified earlier, the exact shape of the cross-sections of the different elements can vary according to diverse variant embodiments and the terms relative to the diameters or to the conicity of the chamber or the internal diameter of the filter (inter alia) are utilise for illustrating variants, but those skilled in the art will appreciate the adaptations which can be made from the forms illustrated here, such as for example square or rectangular cross-sections, in particular with inclined walls for fitting the profile described by the various sizes of the diverse orifices. This filter (15) is preferably made of porous material to allow circulation of the air in the material. Furthermore, the porous material present in the filter(s) (15, 15a, 15b) is preferably an open-weave material (having open or semi-open alveoli or any other intermediate). For instance, the filter can comprise foam of polyurethane or other plastic material, with open alveoli (that is, intercommunicating alveoli so as to facilitate circulation of air through the material: an alveola communicating with its neighbour). The annular volume and the porosity index of the filter (15) are tuned as a function of the sound frequencies to be attenuated by the silencer (1). Therefore, just as when the chamber (10) is empty and attenuates various frequencies as a function of its volume, as in the embodiment illustrated in FIG. 2, the filter (15) attenuates various frequencies as a function of the annular volume which it fills, though the attenuation here is also a function of the porosity index of the filter (15). In certain variant embodiments, the chamber (10) comprises several filters (15a, 15b) of different densities. In particular, in a preferred variant, the density is increasing in the direction of the admission orifice (330) of the turbine (T), as is particularly visible in FIG. 3 showing an embodiment comprising 2 filters. In other variant embodiments, one and the same filter with variable density can be considered. Preferably, this density of the filter will be growing in the direction of the admission orifice (330). Other variant embodiments comprising a single filter of constant density but substantially tapered shape such that part of the filter is more compressed than the rest inside the chamber, resulting from variable density of the filter inside the chamber. Also, according to various variant embodiments, the filters can be separated or not by a wall. These filters (15a, 15b) are also of annular shape and comprise at least one porous material. As previously, the annular volume and the porosity indices of the filters (15) are tuned as a function of the sound frequencies to be attenuated by the silencer (1). In various variants, the filter(s) (15, 15a, 15b) substantially fills (or fill) the annular volume of the chamber (10), as illustrated in FIGS. 2 and 3, but an intermediary configuration can be considered, with an empty annular volume and one or more annular volume(s) comprising at least one filter.

Figure 5A:
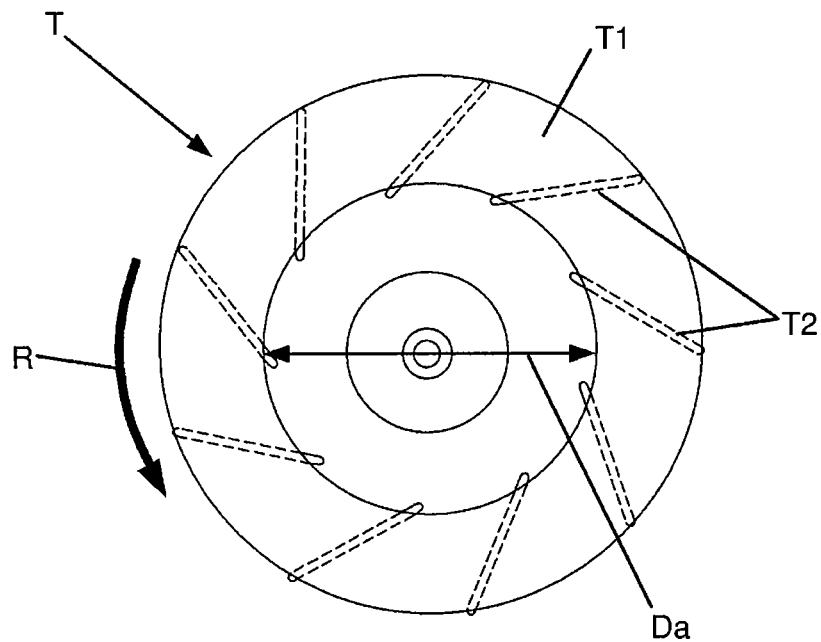
FIGS. 5A and 5B illustrate opposite transparent views, respectively of a turbine known from the prior art and a turbine improved according to certain embodiments of the invention.

FIG. 5A illustrates a centrifugal turbine (T) known from the prior art. This turbine (T) is fitted with a flange (T1) covering the blades (T2) and guiding the aspirated air in between the blades to the circumference of the turbine. The blades (T2) are per se oriented towards the interior of the turbine, in the direction of rotation (R) of the turbine. This orientation of the blades is such that between 2 blades, the flow section at the centre the turbine is less than the flow section at the periphery. The flange (T1) comprises, in its centre, an admission orifice of determined diameter. As mentioned previously, this diameter serves as reference for the air admission and will be defined here as the air admission diameter (Da). Other types of turbines known from the prior art do not comprise a flange, but a wall located upstream plays the same role and limits the entry of air to an admission diameter (Da) of an admission orifice of this wall, as mentioned previously. Therefore, the term admission diameter (Da) will be used here to define this general notion of air admission to the turbine, whether it is fitted with a flange or not (even if it is centrifugal or not). The disadvantage of this type of turbine of the prior art is that it generates noise. There is therefore provision to improve the drying appliance according to the invention by installing therein an improved turbine of the type of that illustrated in FIGS. 5B, 6A and 6B. In this improved turbine (T) according to the invention, the admission diameter (Da) has been reduced (as evident by comparison of FIGS. 5A and 5B), in order to reduce the noise generated. It will be noted in the figures that the leading edge of the blades (their central end) protrudes inside the central orifice of the flange. However, this reduction in diameter causes a reduction of the flow (delivery rate) of air. To conserve satisfactory airflow power, in certain embodiments, the peripheral end of the blades (T2) can be curved in the direction of the direction of rotation (R) of the turbine. Therefore, the pressure generated by the turbine (T) is augmented and compensates the loss of airflow resulting from the reduction of the admission diameter. In certain variant embodiments (not illustrated), the central end of the blades (T2) can also be curved, but in the direction inverse to the direction of rotation (R) of the turbine (T). These embodiments of the improved turbine, comprising reduced admission diameter (Da) and curving at least of the peripheral end of the blades (T2) helps reduce the noise generated by the turbine while conserving satisfactory airflow power. Therefore, since the aim of the present invention is to reduce generated noise, a drying appliance comprising such an improved turbine is also the subject matter of the present invention. FIG. 6A shows a perspective view of the improved turbine (T) according to the invention. This turbine (T) comprises an axis (T4) by which it is driven in rotation and this axis is fitted with a hub (T5) of substantially tapered form, or substantially having the form of a corolla, a tulip or a bell of curved profile flaring towards the leading edge of the blades, guiding the aspirated airflow towards the blades (T2).

The blades (T2) are mounted on a disc (T3) closing the face of the turbine located to the side of the motor. As particularly visible in FIG. 6B, the blades (T2) of the improved turbine of the hair dryer according to certain embodiments of the invention are curved to improve the exit pressure of the turbine. Therefore, the aspirated air is thrust towards the blades (T2) by the internal hub (T5), then guided in the flow section growing between the blades (T2), and pushed by the curved peripheral end of the blades (T2) allowing better pressure.

FIG. 7 illustrates a last refinement of the invention, which will be made to the silencer and/or the hair dryer according to various embodiments of the invention. This refinement consists of adding to the silencer, upstream of the admission orifice, an aerodynamic ball (or bead or drop) (G) reducing perturbation in the area around the inlet of the turbine (T). This ball (G) can, as illustrated in FIG. 7, substantially have the form of a drop of water, that is, comprise a substantially spherical portion and, in the direction of the inlet of the turbine, a substantially conical portion. This ball will be centred relative to the admission orifice (and/or to the intake orifice of the turbine). In certain variant embodiments, the spherical portion will be made of a smooth material, whereas the conical portion will be made of porous material (foam, for example). Other simpler variants in which the two portions are made of identical material can naturally be considered. In the example illustrated in FIG. 7, this ball is fixed by feet (332). For instance, as mentioned previously, the admission orifice can be fitted with a grille (331, FIG. 7) comprising feet or ribs (332) preventing penetration by fingers (children's ideally). These ribs (332) can therefore form fixing of the ball (G) upstream of the admission. This fixing can be conceivable whether there is a grille or not at this level and other types of fixing can of course be adapted, especially by minimising turbulence in the area around the turbine. It will be noted, as is particularly visible in FIG. 7, that the diameter (De) of the intake orifice has been augmented to compensate obstruction of the intake orifice (110) by the ball (G).

Therefore, it is understood that the diverse variant embodiments produce a drying appliance (3) which is very silent due to the presence of the silencer (1), of a silent turbine (T) and a ball (G) upstream of the admission of the turbine, the silencer (1) capable of being fitted with sound-absorbent material. It is easily understood that the invention provides numerous embodiments whereof examples are described here and that these examples are illustrative and can be combined, unless it is evident that they are incompatible. Therefore, the scope of the invention extends to various combinations of the variants described and to the evident adaptations familiar to those of skills in the art.

It must be evident for those skilled in the art that the present invention permits embodiments in numerous other specific forms without departing from the field of application of the invention as claimed. As a consequence, the present embodiments must be considered by way of illustration, but can be modified in the field defined by the scope of the attached claims, and the invention must not be limited to the details given hereinabove.

What is claimed is:

1. A silencer for an appliance comprising:
    at least one casing comprising an inlet end, an outlet end, and at least one motor for rotatably driving at least one turbine for sucking in air via at least one admission orifice at the level of the inlet end upstream of the turbine, said at least one admission orifice having a first diameter, and expelling said air downstream of the turbine via at least one outlet orifice at the level of the outlet end,
    wherein said silencer comprises at least one chamber having a length and mounted substantially tightly upstream of the admission orifice and having an inlet orifice having a second diameter for aspiration of air upstream of the chamber,
    wherein said chamber has a third diameter greater than the first diameter of the admission orifice and the second diameter of the inlet orifice, and
    wherein said length and said third diameter of the chamber are of such a size so as to define a volume tuned as a function of the sound frequencies to be attenuated by the silencer.

2. The silencer according to claim 1,
    wherein the chamber comprises at least one noise filter of annular shape and comprising at least one porous material, and
    wherein the noise filter has an annular volume and a porosity index tuned as a function of the sound frequencies to be attenuated by the silencer.

3. The silencer according to claim 1,
    wherein the chamber comprises several noise filters of increasing density in the direction of the admission orifice of the turbine, and of annular shape and comprising at least one porous material, and
    wherein the noise filters have an annular volume and porosity indices tuned as a function of the sound frequencies to be attenuated by the silencer.

4. The silencer according to claim 2, wherein the at least one noise filter substantially fills an annular volume of the chamber defined between the third diameter and one of the first and second diameters of the chamber.

5. The silencer according to claim 2, wherein the porous material present in the at least one filter is a material having open alveoli.

6. The silencer according to claim 1, wherein the chamber is cylindrical, tapered, or polygonal in cross-section.

7. The silencer according to claim 1, wherein the silencer comprises fixing means on the casing of the drying appliance at the level of the inlet end for attaching the silencer to the casing.

8. The silencer according to claim 1, wherein the silencer is equipped with a cover upstream of the inlet orifice of the chamber, the cover comprising fixing means on the silencer, in the vicinity of the inlet orifice for attachment of the cover.

9. The silencer according to claim 8, wherein the cover is fitted with at least one air filter for filtering particles.

10. The silencer according to claim 8, wherein the silencer further comprises;
    detachable fixing means on the casing identical to detachable fixing means of the cover on the casing of the appliance, at the level of the inlet end, and
    in the vicinity of the inlet orifice, means for anchoring the fixing means of the cover, such that the silencer can be interposed between the casing and the cover.

11. The silencer according to claim 1, wherein the silencer is one piece with the casing, at the level of the inlet end.

12. A silent hair dryer comprising:
    at least one casing, said casing having an inlet end, an outlet end, and at least one motor rotatably driving at least one turbine sucking in air via at least one admission orifice upstream of the turbine and expelling said air via at least one outlet orifice downstream of the turbine, said at least one admission orifice having a first diameter; and
    a silencer comprising at least one chamber having a length and mounted substantially tightly upstream of the admission orifice and having an inlet orifice having a second diameter for aspiration of air upstream of the chamber, wherein said chamber has a third diameter being greater than the first diameter of the admission orifice and the second diameter of the inlet orifice, and wherein said length and said third diameter of the chamber are of such a size so as to define a volume tuned as a function of the sound frequencies to be attenuated by the silencer.

13. The silent hair dryer according to claim 12, wherein the silencer is in one piece with the casing at the level of the inlet end.

14. The silent hair dryer according to claim 12, wherein the silencer is detachably fixed on the casing at the level of the inlet end.

15. The silent hair dryer according to claim 12, wherein the dryer comprises fixing means for detachably mounting a cover on the casing at the level of the inlet end; and wherein the silencer comprises detachable fixing means for detachably fixed the silencer on the casing identical to the detachable fixing means of the cover; and in the vicinity of the inlet orifice, means for anchoring said fixing means of the cover such that the silencer can be interposed between the casing and the cover.

16. The silent hair dryer according to claim 12, wherein said dryer further comprises:

a silent turbine comprising said admission orifice having the first diameter constructed so as to decrease noise generated by the turbine and comprising blades having a curved peripheral end in a direction of rotation of the turbine so as to improve the pressure generated by the turbine to thereby compensate flow loss resulting from the first diameter of the turbine.

17. The silent hair dryer according to claim 12, wherein said dryer comprises an aerodynamic ball placed upstream of the admission orifice of the turbine for minimizing air perturbations entering the turbine and reducing a sound level of the hair dryer.

18. The silencer according to claim 3, wherein the at least one noise filter substantially fills an annular volume of the chamber defined between the third diameter and one of the first and second diameters of the chamber.

19. The silencer according to claim 3, wherein the porous material present in the at least one filter is a material having open alveoli.

* * * * *